United States Patent [19]
Arhancet

[11] Patent Number: 5,859,280
[45] Date of Patent: Jan. 12, 1999

[54] METHODS FOR INHIBITING THE POLYMERIZATION OF VINYL MONOMERS

[75] Inventor: Graciela B. Arhancet, Katy, Tex.

[73] Assignee: BetzDearborn Inc., Trevose, Pa.

[21] Appl. No.: 886,626

[22] Filed: Jul. 1, 1997

[51] Int. Cl.$^6$ .......................... C07C 59/76; C07C 59/84; C07C 59/86
[52] U.S. Cl. .......................... 558/462; 558/463; 585/507; 585/520; 585/614; 585/615
[58] Field of Search .................. 558/462, 463; 585/520, 507, 614, 615

[56] References Cited

U.S. PATENT DOCUMENTS

| | | | |
|---|---|---|---|
| 3,407,240 | 10/1968 | Sakashita | 260/666.5 |
| 4,720,566 | 1/1988 | Martin | 558/306 |
| 5,159,106 | 10/1992 | Ritter et al. | 560/224 |
| 5,171,888 | 12/1992 | Roling | 562/598 |
| 5,457,216 | 10/1995 | Kleinknecht | 549/408 |
| 5,461,124 | 10/1995 | Ritter et al. | 526/84 |

FOREIGN PATENT DOCUMENTS

| | | |
|---|---|---|
| 163428 | 6/1976 | Czechoslovakia . |
| 0705872 A2 | 9/1995 | European Pat. Off. . |

OTHER PUBLICATIONS

Chem Abstracts 89:110589u, The Effects of Alpha–tocopherol and it's Derivative on Polymerization of Methyl Metharylate; Enmanji, Takahashi, and Kusakawa, 1978.

Chem Abstracts 103:142453u, The Effects of alpha–tocopherol on Polymerization of Methyl Methacrylate, Enmanji, 1985.

Chemical abstracts 99:23075, abstract of JP 58035131, Mar. 1, 1983.

Primary Examiner—Alan L. Rotman
Assistant Examiner—D. Margaret M. Mach
Attorney, Agent, or Firm—Alexander D. Ricci; Steven D. Boyd

[57] ABSTRACT

An alpha-tocopherol is disclosed as a polymerization inhibitor effective against vinyl monomer polymerization. Alpha-tocopherol was found to inhibit polymerization of acrylonitrile and diolefines such as isoprene and butadiene. Alpha-tocopherol was found to interact synergistically with hydroquinone in inhibiting polymerization of acrylonitrile.

13 Claims, No Drawings

METHODS FOR INHIBITING THE POLYMERIZATION OF VINYL MONOMERS

FIELD OF THE INVENTION

The present invention relates to methods for inhibiting the polymerization of vinyl monomers. More particularly, the present invention relates to method for inhibiting polymerization of vinyl monomers during processing and storage of the vinyl monomers.

BACKGROUND OF THE INVENTION

Polymerizable vinyl monomers undesirably polymerize during various stages of the manufacturing, processing, handling, storage and use thereof. It is well known that vinyl monomers readily polymerize and that such polymerization increases with concurrent temperature increases.

Common industrial methods for producing vinyl monomers include a variety of purification processes, including distillation to remove impurities. Unfortunately, purification operations carried out at elevated temperatures result in an increased rate of undesired polymerization. Polymerization such as thermal polymerization during the monomer purification process results not only in loss of desired monomer end product, but also in loss of production efficiency caused by polymer formation or agglomeration on process equipment. In heat requiring operations, such agglomeration adversely effects heat transfer efficiency.

Vinyl monomers may polymerize when left in storage tanks and during transportation at temperatures as low as room temperature. To prevent this polymerization from taking place, vinyl monomers are frequently treated with polymerization inhibitors.

A variety of compositions and methods have been proposed for inhibiting uncontrolled polymerization of vinyl monomers. For example, polymerization of acrylonitrile can be inhibited with phenothiazine, hydroquinone (HQ), methyl ether of hydroquinone (MEHQ), benzoquinone, methylene blue and combinations of hydroxyethylamine and phenylalene diamine. See, for example, U.S. Pat. No. 4,720, 566. Polymerization inhibition of isoprene can be achieved by addition of tert-butylcatechol (TBC). TBC is also employed commercially to inhibit storage polymerization of butadiene and styrene.

U.S. Pat. No. 4,561,124 discloses the use of vitamin E as an inhibitor against premature polymerization initiation in reactive systems capable of undergoing a free radical initiated polymerization, which system before and/or after the polymerization thereof are placed in tissue contact with a living body. The reactive composition of concern in U.S. Pat. No. 4,561,124 are monocomponent or multicomponent medical and/or dental-medical adhesives, cements, or fillers based on conventional monofunctional and/or polyfunctional olefinically unsaturated compounds, particularly acrylic acid and/or methacrylic acids or derivatives thereof.

U.S. Pat. No. 5,159,106 discloses the use of a finely dispersed liquid phase containing inhibitors to stabilize reactive liquids in the production of (meth)acrylic acid. The finely dispersed liquid phase forms a continuous liquid film on the inner wall surfaces of the equipment. The inhibitors disclosed include hydroquinone, sterically hindered hydroquinone such as di-tert-butylhydroquinone and sterically hindered phenol compounds of the tocopherol type.

SUMMARY OF THE INVENTION

The present inventor has discovered that alpha-tocopherol (Vitamin E) is highly effective against vinyl monomer polymerization under various conditions. In particular, alpha-tocopherol was found to inhibit polymerization of isoprene and acrylonitrile under accelerated conditions that simulate processing and storage conditions. Alpha-tocopherol was also found to interact synergistically with hydroquinone in inhibiting polymerization of acrylonitrile under simulated processing and storage conditions.

DETAILED DESCRIPTION OF THE INVENTION

The present invention relates to methods for inhibiting the polymerization of vinyl monomers comprising adding an effective inhibiting amount of alpha-tocopherol alone or in combination with hydroquinone.

The alpha-tocopherol or combination of alpha-tocopherol and hydroquinone are effective at inhibiting the polymerization of vinyl monomers during processing, storage, or transportation conditions. The present inventor anticipates that the methods of the present invention can inhibit polymerization of vinyl monomers during the processing thereof. These processing conditions, such as purification and distillation processes, typically employ heat and will often cause fouling of the monomer.

The vinyl monomers of the present invention are characterized by a CH2=CH— grouping and are highly reactive and polymerize easily. They include vinyl chloride, vinyl acetate and similar esters; styrene, methylmethacrylate and acrylonitrile as well as isoprene.

For purposes of the present invention, the term "effective amount" refers to the amount of alpha-tocopherol or combination of alpha-tocopherol and hydroquinone necessary to inhibit polymerization of vinyl monomers. This amount will vary according to the conditions under which the ethylenically unsaturated monomer is subjected during storage and handling thereof. At higher temperatures and higher monomer contamination, larger amounts of polymerization inhibiting compound are generally required.

Preferably, the effective amount of alpha-tocopherol or combination of alpha-tocopherol and hydroquinone added to the vinyl monomer ranges from about 1 part to about 10,000 parts per million parts monomer. More preferably, the amount of alpha-tocopherol or combination of alpha-tocopherol and hydroquinone added to the monomer ranges from about 1 part to about 500 parts per million parts monomer. The ratio of alpha-tocopherol to hydroquinone can range from about 1 to 9 to about 9 to 1. The preferred ratio is about 1 to 1.

The alpha-tocopherol or combination of alpha-tocopherol and hydroquinone may be added to the vinyl monomer as either a dispersion or as a solution using a suitable liquid carrier or solvent. Any solvent that is compatible with the treatment and the vinyl monomer may be employed.

The invention will now be described with reference to a number of specific examples which are to be regarded solely as illustrative, and not as restricting the scope of the present invention.

EXAMPLES

Testing was performed to determine the effectiveness of the present invention at inhibiting the polymerization of vinyl monomers of isoprene and acrylonitrile.

Tests were conducted in a stainless steel pressure vessel (constructed in accordance with ASTM D 252-88) fitted with a glass sample container and stopper, a stem, a pressure gauge with a continuous recorder, and the appropriate valves and fittings. A solution of vinyl monomer to be tested and the designated polymerization inhibition treatments were placed in the glass sample container and inside the pressure vessel. The vessel was closed, filled with oxygen at 100 psig and heated in a water bath at 100° C. The pressure was recorded continuously until a break point in the pressure-time curve (i.e., steepest slope of the curve) was reached. The induction time was calculated as the time elapsed between the placing of the vessel in the bath and the break point. The results of this testing are reported.

EXAMPLE I

The above-described procedure was employed with solutions of 10 milliliters of isoprene in 40 milliliters of heptene and the treatment designated. Table 1 summarizes the results.

TABLE 1

| Treatment | Dose (ppm) | Induction Time (min.) |
| --- | --- | --- |
| Blank | — | 25 |
| TBC | 10 | 40 |
| α-tocopherol | 10 | 40 |
| α-tocopherol | 50 | 89 |

TBC is tert-butyl catechol

The results demonstrate that the compounds of the present invention are effective at inhibiting the polymerization of vinyl monomer (isoprene) under conditions approximating storage. The commercially available inhibitor TBC proved similar in performance, but is significantly more toxic than the inventive material.

EXAMPLE II

Uninhibited acrylonitrile (10 milliliters) was placed in a 50 milliliter pressure glass tube fitted with a stopper. The desired treatment was added, the tube closed and immersed in an oil bath at 110° C. Every thirty minutes the tubes were inspected for turbidity or the presence of polymer and the elapsed time was recorded. Tables 2 and 3 summarize the results.

TABLE 2

| Treatment | Dose (ppm) | Induction Time (min.) |
| --- | --- | --- |
| Blank | — | 60 |
| HQ | 1 | 270 |
| HQ | 2.5 | 350 |
| HQ | 5 | 560 |
| α-tocopherol | 1 | 450 |
| α-tocopherol | 2.5 | 600 |
| α-tocopherol | 5 | 1300 |

TABLE 3

| Treatment | Dose (ppm) | Induction Time (min.) |
| --- | --- | --- |
| Blank | — | 50 |
| HQ | 1 | 100 |
| α-tocopherol | 1 | 360 |
| α-tocopherol/HQ | 1 | 720 |

HQ is hydroquinone
***Three run average

These results demonstrate that the compounds of the present invention are effective at inhibiting the polymerization of vinyl monomers (acrylonitrile) under conditions approximating storage. The commercially available inhibitor, hydroquinone, proved less effective than the inventive materials. Furthermore, a combination of the inventive material and hydroquinone exhibited synergistic activity.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

What is claimed is:

1. A method for inhibiting polymerization of vinyl monomers consisting essentially of unsaturated vinyl monomers during processing, storage, and transportation comprising adding to the vinyl monomers an effective polymerization inhibiting amount of an alpha-tocopherol.

2. The method of claim 1 wherein said alpha-tocopherol is added to said monomers in an amount ranging from about 1 to about 10,000 parts per million parts of monomer.

3. The method of claim 1 wherein said alpha-tocopherol is added to said vinyl monomers in an amount ranging from about 1 to about 500 parts per million parts of vinyl monomer.

4. The method of claim 3 wherein said vinyl monomer is acrylonitrile.

5. The method of claim 4 wherein said polymerization inhibiting amount of an alpha-tocopherol further comprises hydroquinone.

6. The method of claim 5 wherein the ratio of alpha-tocopherol to hydroquinone ranges from about I to 9 to about 9 to 1.

7. The method of claim 1 wherein said vinyl monomer is a diolefin selected from the group consisting of isoprene and butadiene.

8. The method of claim 7 wherein said alpha-tocopherol is added to said vinyl monomers in an amount ranging from about 1 to about 1000 parts per million parts of vinyl monomer.

9. The method of claim 7 wherein said vinyl monomer is exposed to oxygen atmospheres.

10. A method of inhibiting polymerization of unsaturated vinyl monomers comprising adding to said unsaturated vinyl monomers an effective polymerization inhibiting amount of a combination of (a) an alpha-tocopherol and (b) hydroquinone.

11. The method of claim 10 wherein the ratio of alpha-tocopherol to hydroquinone ranges from about 1 to 9 to about 9 to 1.

12. The method of claim 10 when said vinyl monomer is selected from the group consisting of acrylonitrile and diolefins.

13. The method of claim 12 wherein said diolefins are selected from the group consisting of isoprene and butadiene.

* * * * *